United States Patent
Bae et al.

(10) Patent No.: US 10,374,074 B2
(45) Date of Patent: Aug. 6, 2019

(54) FLEXIBLE BIMODAL SENSOR

(71) Applicants: SAMSUNG ELECTRONICS CO., LTD., Suwon-si (KR); RESEARCH & BUSINESS FOUNDATION SUNGKYUNKWAN UNIVERSITY, Suwon-si (KR)

(72) Inventors: Jihyun Bae, Seoul (KR); Nae-Eung Lee, Seoul (KR); Doil Kim, Suwon-si (KR); Thanh Tien Nguyen, Yongin-si (KR); Sunghoon Lee, Seoul (KR); Sanghun Jeon, Seoul (KR)

(73) Assignees: SAMSUNG ELECTRONICS CO., LTD., Suwon-si (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 421 days.

(21) Appl. No.: 15/200,293

(22) Filed: Jul. 1, 2016

(65) Prior Publication Data

US 2017/0000358 A1    Jan. 5, 2017

(30) Foreign Application Priority Data

Jul. 2, 2015    (KR) .......................... 10-2015-0094939

(51) Int. Cl.
*H01L 29/78*        (2006.01)
*A61B 5/0205*       (2006.01)
(Continued)

(52) U.S. Cl.
CPC .......... *H01L 29/78* (2013.01); *A61B 5/02055* (2013.01); *A61B 5/02444* (2013.01);
(Continued)

(58) Field of Classification Search
CPC ....... H01L 27/222; H01L 43/08; H01L 43/10; H01L 43/12; H01L 29/78
See application file for complete search history.

(56) References Cited

U.S. PATENT DOCUMENTS 8,426,900 B2    4/2013    Ahn et al.
8,758,985 B2    6/2014    Lee et al.
(Continued)

FOREIGN PATENT DOCUMENTS

KR    10-2007-0070693 A    7/2007
KR    10-2010-0038961 A    4/2010
(Continued)

OTHER PUBLICATIONS

Forbes, "Apple May Bring 'Force Touch' to New iPhones" Tech, Mar. 11, 2015 (one page).
(Continued)

*Primary Examiner* — Allan R Wilson
(74) *Attorney, Agent, or Firm* — Sughrue Mion, PLLC

(57) ABSTRACT

A flexible bimodal sensor includes a gate electrode; a flexible substrate; a source electrode disposed on the flexible substrate; a drain electrode disposed on the flexible substrate apart from the source electrode; a channel layer disposed on the source electrode and the drain electrode and a portion of the flexible substrate between the source electrode and the drain electrode; and a gate insulating layer comprising a plurality of protrusions, the gate insulating layer being disposed on the channel layer and arranged between the channel layer and the gate electrode. The drain electrode outputs a current signal simultaneously indicating a temperature value and a pressure value sensed by the flexible bimodal sensor.

18 Claims, 5 Drawing Sheets

(51) Int. Cl.
*G01L 9/00* (2006.01)
*G01K 7/16* (2006.01)
*A61B 5/024* (2006.01)
*A61B 5/01* (2006.01)
*A61B 5/021* (2006.01)
*A61B 5/0245* (2006.01)
*A61B 5/00* (2006.01)

(52) U.S. Cl.
CPC .............. *G01K 7/16* (2013.01); *G01L 9/0051* (2013.01); *A61B 5/01* (2013.01); *A61B 5/0245* (2013.01); *A61B 5/02108* (2013.01); *A61B 5/6802* (2013.01); *A61B 2562/028* (2013.01); *A61B 2562/0247* (2013.01); *A61B 2562/0276* (2013.01); *A61B 2562/046* (2013.01); *A61B 2562/125* (2013.01)

(56) References Cited

U.S. PATENT DOCUMENTS

| | | |
|---|---|---|
| 9,752,941 B2 | 9/2017 | Jeon et al. |
| 2003/0080384 A1* | 5/2003 | Takahashi ............... C30B 25/02 257/347 |
| 2004/0124469 A1* | 7/2004 | Makita .................... H01L 27/12 257/347 |
| 2012/0223311 A1* | 9/2012 | Endo .................... H01L 29/7869 257/57 |
| 2013/0140611 A1 | 6/2013 | Kim et al. |
| 2016/0351724 A1* | 12/2016 | Zhao ..................... H01L 29/786 |
| 2018/0301565 A1* | 10/2018 | Liu ................... H01L 29/78627 |

FOREIGN PATENT DOCUMENTS

| | | |
|---|---|---|
| KR | 10-2012-0113916 A | 10/2012 |
| KR | 10-2014-0032093 A | 3/2014 |
| KR | 10-2014-0106296 A | 9/2014 |

OTHER PUBLICATIONS

Do-Il Kim et al., "A Sensor Array Using Multifunctional Field-effect Transistors with Ultrahigh Sensitivity and Precision for Bio-monitoring" Scientific Reports, vol. 5, Jul. 30, 2015 (pp. 1-11).

Yiftach Katzir et al., "A plasma microlens for ultrashort high power lasers" Applied Physics Letters, vol. 95, Jul. 20, 2009 [retrieved from https://doi.org/10.1063/1.3184788 ] (4 pages total).

Nguyen Thanh Tien et al., "A Flexible Bimodal Sensor Array for Simultaneous Sensing of Pressure and Temperature" Advanced Materials, vol. 26, 2014 (pp. 796-804).

* cited by examiner (a)  (b)  (c)

FLEXIBLE BIMODAL SENSOR

CROSS-REFERENCE TO RELATED APPLICATION

This application claims priority from Korean Patent Application No. 10-2015-0094939, filed on Jul. 2, 2015 in the Korean Intellectual Property Office, the disclosure of which is incorporated herein by reference in its entirety.

BACKGROUND

1. Field

Apparatuses and methods consistent with exemplary embodiments relate to flexible bimodal sensors having a three-dimensional (3D) microstructure.

2. Description of the Related Art

A physical sensor, for example, a pressure sensor generally has a two-dimensional (2D) thin-film type structure. A pressure sensor of the related art has a pressure sensing range of a few hundred Kilo-Pascal or greater and is used for detecting a relatively high pressure.

However, in order to apply a pressure sensor to smart electronic devices, for example, wearable electronics, a highly sensitive pressure sensor may be needed to measure biorhythm changes of a human body in real-time. To this end, there is a need to manufacture a sensor device having a three-dimensional (3D) structure that may induce a large mechanical and electrical change even at a small pressure unlike a 2D structure of the related art.

Also, since a pressure detecting material is very sensitive to temperature, temperature interference may not be easily avoided. In order to simultaneously detect both temperature and pressure, a temperature sensor and a pressure sensor are integrated on the same substrate, and thus, a volume of a wearable electronic is increased.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide flexible bimodal sensors having a 3D microstructure.

According to an aspect of an exemplary embodiment, there is provided a flexible bimodal sensor including: a gate electrode; a flexible substrate; a source electrode disposed on the flexible substrate; a drain electrode disposed on the flexible substrate apart from the source electrode; a channel layer disposed on the source electrode and the drain electrode and a portion of the flexible substrate between the source electrode and the drain electrode; and a gate insulating layer comprising a plurality of protrusions, the gate insulating layer being disposed on the channel layer and arranged between the channel layer and the gate electrode. The drain electrode may output a current signal simultaneously indicating a temperature value and a pressure value sensed by the flexible bimodal sensor.

The plurality of protrusions of the gate insulating layer may be protruded in a direction away from the gate electrode, and an air gap may exist between two adjacent protrusions of the plurality of protrusions.

The flexible bimodal sensor may further include a processor configured to obtain a channel trans-conductance value and an equilibrium voltage in the gate insulating layer from the current signal, and determine the temperature value and the pressure value based on an equation indicating a relationship between the channel trans-conductance value, the equilibrium voltage, the temperature value, and the pressure value.

The channel layer may include one of silicon, an organic semiconductor, and a semiconductor oxide.

The flexible bimodal sensor may further include an encapsulating layer that covers the channel layer and is disposed between the channel layer and the gate insulating layer.

The encapsulating layer may include one of an organic material comprising tetratetracontane (TTC) or methylcycloheane (MCH), an inorganic oxide comprising $Al_2O_3$ or $HfO_2$, and a stack structure in which the organic material and the inorganic oxide are stacked.

The gate insulating layer may include a base having a predetermined thickness and the plurality of protrusions extends from the base towards the channel layer.

The plurality of protrusions may include a plurality of first protrusions formed on a first surface of the base and a plurality of second protrusions formed on a second surface facing the first surface of the base.

The gate insulating layer may include a first material selected from the group consisting of P(VDF_TrFE), P(VDF-TrFE-CFE), P(VDF-TrFE-CtFE), polydimethylsiloxane (PDMS), and polyurethane (PU).

The gate insulating layer may further include inorganic nano-particles distributed in the first material.

The plurality of protrusions of the gate insulating layer may have a pyramid shape or a truncated pyramid shape.

The flexible bimodal sensor may be a plurality of bimodal sensors, and the plurality of bimodal sensors may be arranged in a matrix shape on the flexible substrate.

According to an aspect of another exemplary embodiment, there is provided a flexible bimodal sensor including: a flexible substrate; a gate electrode disposed on the flexible substrate; a gate insulating layer covering the gate electrode on the flexible substrate; a channel layer disposed on the gate insulating layer; and a source electrode disposed on the channel layer; and a drain electrode disposed on the channel layer apart from the source electrode, wherein the gate insulating layer comprises a plurality of protrusions, and the drain electrode outputs a current signal simultaneously indicating a temperature value and a pressure value measured by the flexible bimodal sensor.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
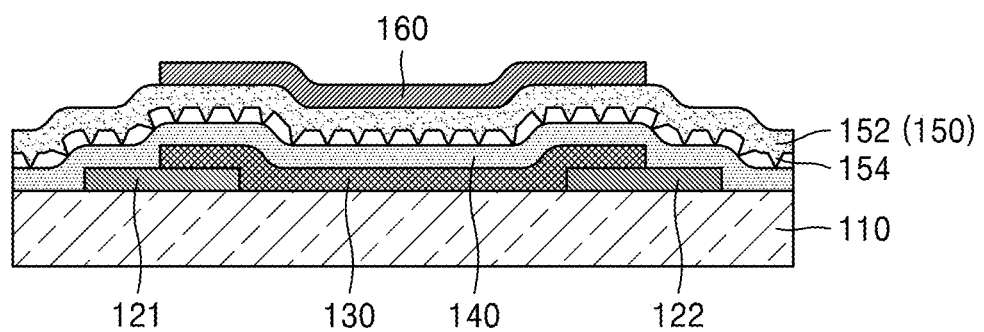
FIG. 1 is a schematic cross-sectional view of a flexible bimodal sensor having a microstructure according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Hereinafter, it will be understood that when an element or layer is referred to as being "on" or "above" another element or layer, the element or layer may be directly on another element or layer or intervening elements or layers.

FIG. 1 is a schematic cross-sectional view of a flexible bimodal sensor 100 that includes a microstructure according to an exemplary embodiment.

Referring to FIG. 1, the flexible bimodal sensor 100 may include a source electrode 121 and a drain electrode 122 that are formed on a flexible substrate 110. The source electrode 121 and the drain electrode 122 are separated from each other on the flexible substrate 110.

A channel layer 130 is formed on the flexible substrate 110 to cover an exposed surface of the flexible substrate 110 between the source electrode 121 and the drain electrode 122. Edges of the channel layer 130 are respectively connected to the source electrode 121 and the drain electrode 122. An encapsulating layer 140 may be further formed on the channel layer 130.

A gate insulating layer 150 is disposed on the encapsulating layer 140. The gate insulating layer 150 may include a plurality of protrusions 154 that protrude towards the channel layer 130 from one side of the gate insulating layer 150. The plurality of protrusions 154 may be formed to contact the encapsulating layer 140. A gate electrode 160 is formed on another side of the gate insulating layer 150. Under the structure, the plurality of protrusions 154 may be protruded in a direction away from the gate electrode 160.

The flexible substrate 110 may be formed of a flexible polymer, such as polyethylene terephthalate (PET), polyimide (PI), polystyrene (PS), polyethersulfone (PES), or polyethylene naphthalate (PEN) or an elastic polymer, such as polydimethylsiloxane (PDMS), polyurethane (PU), Ecoflex®, or Dragon Skin®.

The channel layer 130 and the gate insulating layer 150 may be formed of a multi-stimuli responsive material. The channel layer 130 may be formed of a piezo-thermoresistive organic semiconductor, and the gate insulating layer 150 may be formed of a piezopyroelectric material. Temperature and pressure may be measured from a drain current of the flexible bimodal sensor 100 that is changed according to stimulation, such as pressure and temperature of the gate insulating layer 150 and the channel layer 130.

However, the current exemplary embodiment is not limited thereto. That is, the channel layer 130 may be formed of silicon or a semiconductor oxide, such as zinc oxide, or indium gallium zinc oxide (IGZO). The organic semiconductor may be formed of pentacene. Semiconductor characteristics of an organic semiconductor, such as pentacene may be reduced by being reacted with oxygen or being contaminated by other materials.

The encapsulating layer 140 prevents the organic semiconductor from being reacted with oxygen or being contaminated with other materials. The encapsulating layer 140 may be formed at least to completely cover the organic semiconductor. The encapsulating layer 140 may be formed of an organic material including tetratetracontane (TTC) or methylcycloheane (MCH) or an inorganic oxide that includes $Al_2O_3$ or $HfO_2$. However, the current exemplary embodiment is not limited thereto. For example, the encapsulating layer 140 may have a structure in which the organic material and the inorganic oxide are sequentially stacked on the channel layer 130.

The gate insulating layer 150 includes a base 152 having a predetermined thickness and the plurality of protrusions 154 extending from the base 152. The plurality of protrusions 154 are disposed at a regular interval with predetermined gaps to form a pattern. The gate insulating layer 150 may be formed of a piezopyroelectric material, for example, P(VDF_TrFE), P(VDF-TrFE-CFE), or P(VDF-TrFE-CtFE). However, the current exemplary embodiment is not limited thereto. For example, the gate insulating layer 150 may be formed of PDMS or polyurethane (PU).

The gate insulating layer 150 may include a material selected from the group consisting of P(VDF_TrFE), P(VDF-TrFE-CFE), P(VDF-TrFE-CtFE), PDMS, and PU (hereinafter, referred to as a "first material") as a matrix and inorganic nano-particles distributed in the first material. The inorganic nano-particles may include gallium orthophosphate ($GaPO_4$), langasite ($La_3Ga_5SiO_{14}$), a quartz analogic crystal, barium titanate ($BaTiO_3$), lead titanate ($PbTiO_3$), lead zirconate titanate ($Pb[Zr_xTi_{1-x}]_3, 0 \le x \le 1$), potassium niobate ($KNbO_3$), lithium niobate ($LiNbO_3$), lithium tantalate ($LiTaO_3$), sodium tungstate ($Na_2WO_3$), zinc oxide ($Zn_2O_3$), $Ba_2NaNb_5O_5$, $Pb_2KNb_5O_{15}$, sodium potassium niobate ($(K, Na)NbO_3$), bismuth ferrite ($BiFeO_3$), sodium niobate $NaNbO_3$, bismuth titanate $Bi4Ti_3O_{12}$, or sodium bismuth titanate $Na_{0.5}Bi_{0.5}TiO_3$.

The plurality of protrusions 154 of the gate insulating layer 150 may have a horn shape or a truncated horn shape.

The flexible bimodal sensor 100 may further include a processor and a memory. The processor may calculate temperature and pressure based on a drain current measured from the drain electrode 122 by using equations (e.g., Equations 1 and 2 described below) stored in the memory.

In FIG. 1, it is depicted that the plurality of protrusions 154 of the gate insulating layer 150 is in contact with the encapsulating layer 140. However, the current exemplary embodiment is not limited thereto. For example, the plurality of protrusions 154 may be in contact with the gate electrode 160.

Figure 2:
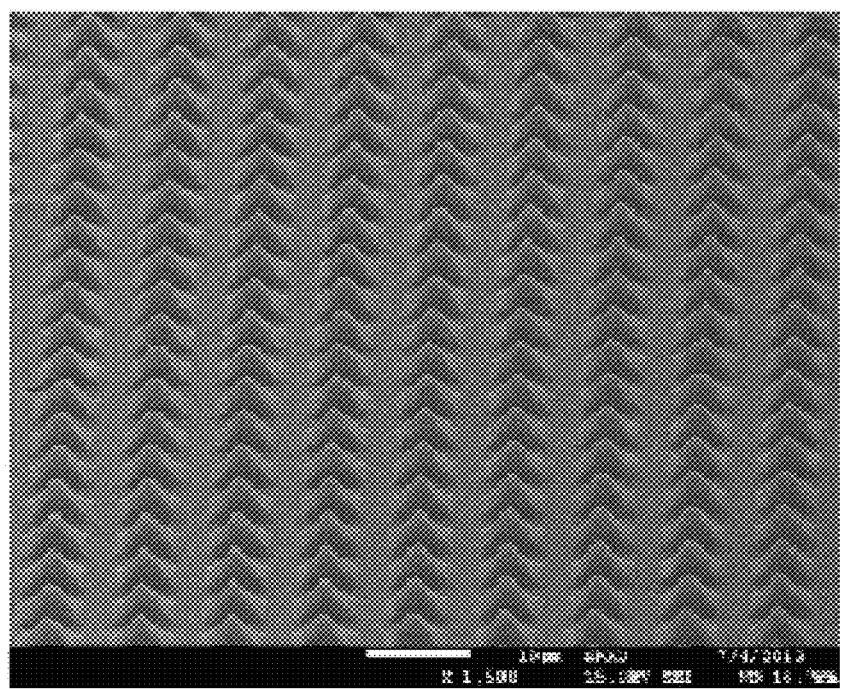
FIG. 2 is a scanning electron microscope (SEM) image of a plurality of protrusions of a gate insulating layer of a flexible bimodal sensor according to an exemplary embodiment.

FIG. 2 is a scanning electron microscope (SEM) image showing a plurality of protrusions of a gate insulating layer of a flexible bimodal sensor according to an exemplary embodiment. Referring to FIG. 2, the plurality of protrusions is regularly formed in a matrix type. FIG. 2 shows that the plurality of protrusions has a pyramid shape.

The gate insulating layer 150 having the plurality of protrusions 154 is formed by spin coating P(VDF_TrFE) on a stamp mold having a concave shape opposite to the shape of the plurality of protrusions 154, heating the stamp mold at a temperature of 140° C. to form a P(VDF_TrFE) crystal, and transferring the P(VDF_TrFE) crystal onto the channel layer 130.

Figure 3:
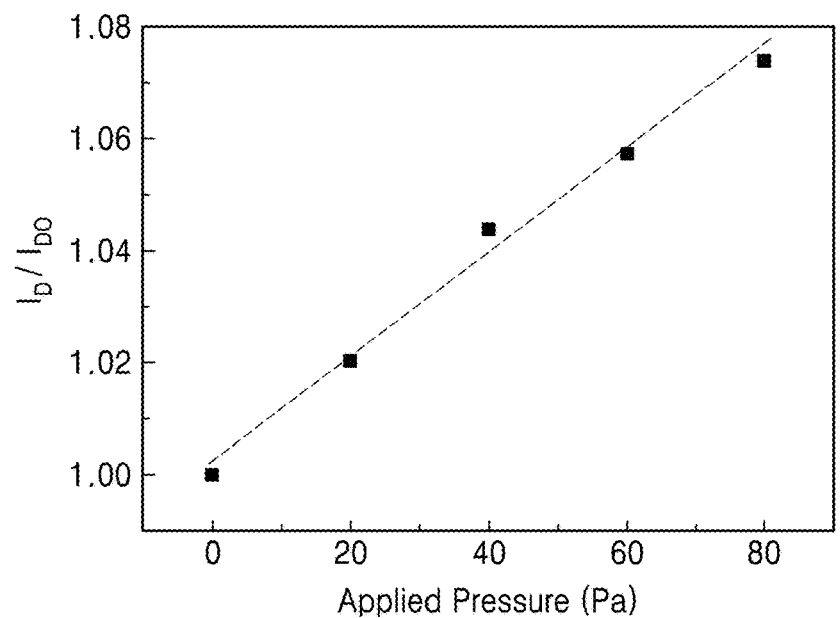
FIG. 3 is a graph showing a pressure sensing sensitivity of a flexible bimodal sensor according to an exemplary embodiment.

FIG. 3 is a graph showing a measured pressure sensing sensitivity of a flexible bimodal sensor by using the P(VDF_TrFE) as the gate insulating layer 150. In order to measure a low pressure range, a drain current was measured after a predetermined weight is applied onto the gate electrode 160 of the flexible bimodal sensor 100.

Referring to FIG. 3, it is known that the drain current $I_D$ of the flexible bimodal sensor 100 increases at a constant rate even at a very low pressure change of 20 Pascal. The flexible bimodal sensor 100 according to an exemplary embodiment has a very high sensitivity at a low pressure, and thus, may be used for measuring bio information (e.g., blood pressure, heart rate, etc.).

Figure 4:
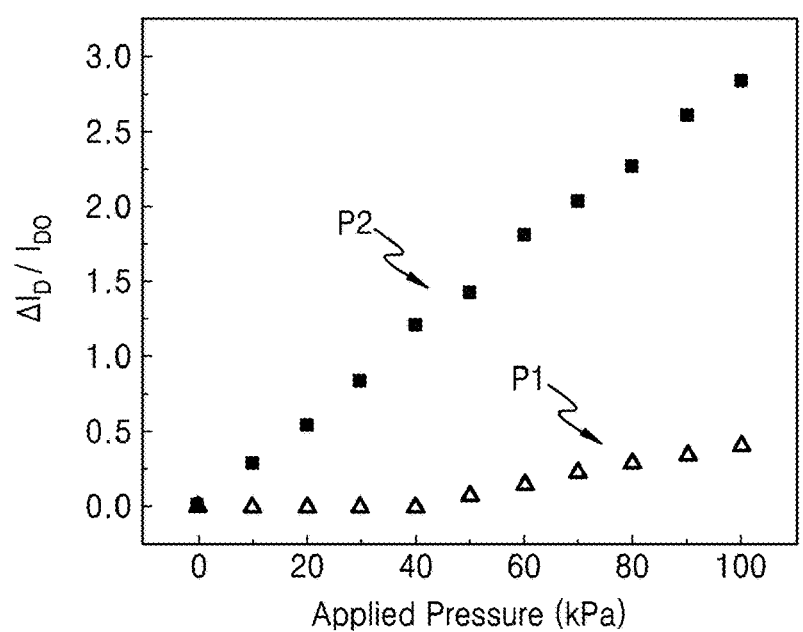
FIG. 4 is a graph for comparing the sensitivity of a sensor of the related art with that of a flexible bimodal sensor according to an exemplary embodiment.

FIG. 4 is a graph showing a comparison of sensitivity between a sensor of the related art and a flexible bimodal sensor according to an exemplary embodiment. The sensor of the related art is different from the flexible bimodal sensor 100 according to the exemplary embodiment in that a gate insulating layer of the sensor of the related art has a flat panel shape without protrusions. In order to measure a drain current, a source is connected to a ground voltage, a voltage of −20 V is applied to the drain, and an alternate current having amplitude of 20 V and 0.3125 Hz is applied to the gate electrode 160. Pressure increases from 10 kPa to 100 kPa.

Referring to FIG. 4, a regression value of plotting data P1 measured by using a sensor of the related art is 0.003 kPa$^{-1}$ and a regression value of plotting data P2 measured by using a flexible bimodal sensor 100 according to the exemplary embodiment is 0.028 kPa$^{-1}$. That is, it is known that the pressure sensitivity of the flexible bimodal sensor 100 according to the exemplary embodiment is approximately 10 times greater than that of the sensor of the related art. Thus, it is understood that, in the flexible bimodal sensor 100 according to the exemplary embodiment, deformation of protrusions having a 3D microstructure is further increased according to the change of pressure, and thus, the pressure sensitivity is increased.

Figure 5:
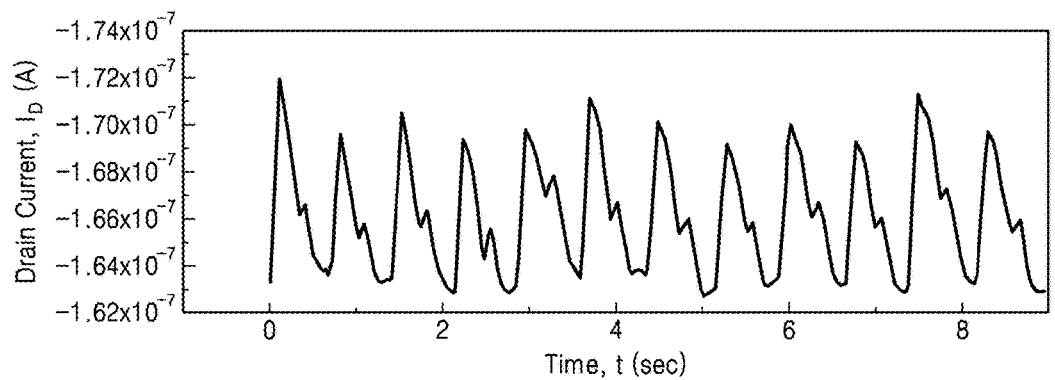
FIG. 5 is a graph showing a pulse wave measured by using a flexible bimodal sensor according to an exemplary embodiment.

FIG. 5 is a graph showing a pulse wave measured by using the flexible bimodal sensor 100 according to an exemplary embodiment. The gate insulating layer 150 is formed of P(VDF_TrFE), and the channel layer 130 is formed of pentacene.

Referring to FIG. 5, in a state that the flexible bimodal sensor 100 is disposed on a radial artery of a wrist, the flexible bimodal sensor 100 detects pressure caused by a pulse wave, and accordingly, a drain current is changed. Referring to FIG. 5, a pulse wave of a drain current has the same shape as a general pulse wave. That is, a measured single pulse wave shows a typical arterial pulse waveform. From the data of FIG. 5, the pulse frequency of an object is approximately 82.

Hereinafter, a method of simultaneously measuring a temperature and pressure by using an alternating current (AC) bias measuring method will be described when two physical stimulations, for example, temperature and pressure are simultaneously applied to the flexible bimodal sensor 100 according to an exemplary embodiment.

A temperature and pressure are measured by using a matrix of measured signal values, for example, drain values.

First, changed values of μC and $V_o$ are measured. A relationship between the measured values and a temperature and pressure to be measured is expressed as Equation 1.

$$\begin{bmatrix} \Delta \mu C \\ \Delta V_0 \end{bmatrix} = \begin{bmatrix} M_1 & M_2 \\ M_3 & M_4 \end{bmatrix} \begin{bmatrix} \Delta P \\ \Delta T \end{bmatrix}$$ [Equation 1]

Here, μC is channel trans-conductance $g_m$. $V_o$ is a voltage remaining in a ferroelectric gate insulating layer when a voltage applied to the ferroelectric gate insulating layer is removed. $V_o$ is also referred to as an equilibrium voltage. $M_1$ and $M_2$ respectively are a piezoresistance coefficient and a thermal resistance coefficient of the pentacene channel. $M_3$ and $M_4$ respectively are a piezoelectric coefficient and a pyroelectric coefficient of a ferroelectric P(VDF_TrFE). When the inverse matrix is used to obtain a temperature T and a pressure P, the equation of Equation 2 below is obtained.

$$\begin{bmatrix} \Delta P \\ \Delta T \end{bmatrix} = \begin{bmatrix} M_1 & M_2 \\ M_3 & M_4 \end{bmatrix}^{-1} \begin{bmatrix} \Delta \mu C \\ \Delta V_0 \end{bmatrix}$$ [Equation 2]

The memory may store at least one of Equations 1 and 2. Further, the memory may store the piezoresistance coefficient M1, thermal resistance coefficient M2, the piezoelectric coefficient M3, and the pyroelectric coefficient M4. When the channel trans-conductance value μC and the equilibrium voltage $V_o$ are measured, the processor may retrieve Equation 1 or 2 from the memory, and may determine the temperature T and the pressure P based on the retrieved Equation 1 or 2.

Accordingly, the variation magnitudes of the temperature and pressure may be extracted from the variations of the measured drain currents according to the characteristics of a field effect transistor.

Figure 6:
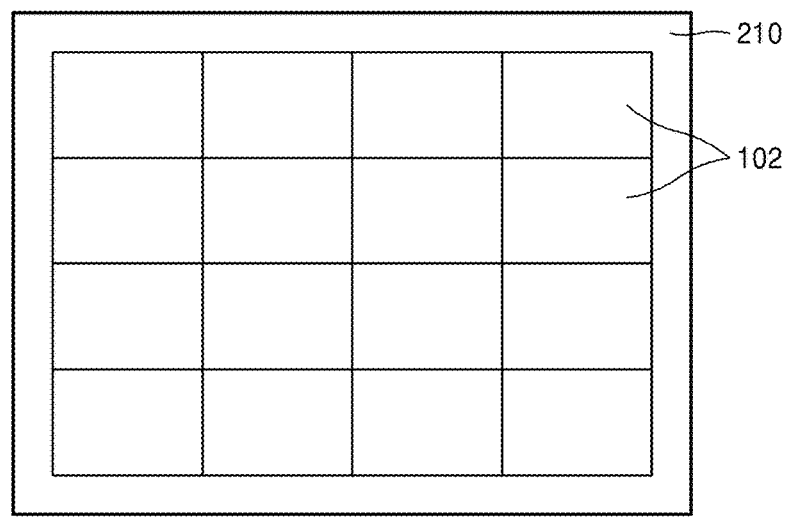
FIG. 6 is a schematic plan view of a flexible bimodal sensor array according to an exemplary embodiment.

FIG. 6 is a schematic plan view of a flexible bimodal sensor array according to an exemplary embodiment.

Referring to FIG. 6, a plurality of flexible bimodal sensors 102 are arranged in a matrix type on a flexible substrate 210. As an example, FIG. 6 shows the flexible bimodal sensors 102 arranged in a 4×4 matrix type. The structure of each of the flexible bimodal sensors 102 may be substantially the same as that of the flexible bimodal sensor 100, and thus, the explanation thereof will not be repeated.

Figure 7:
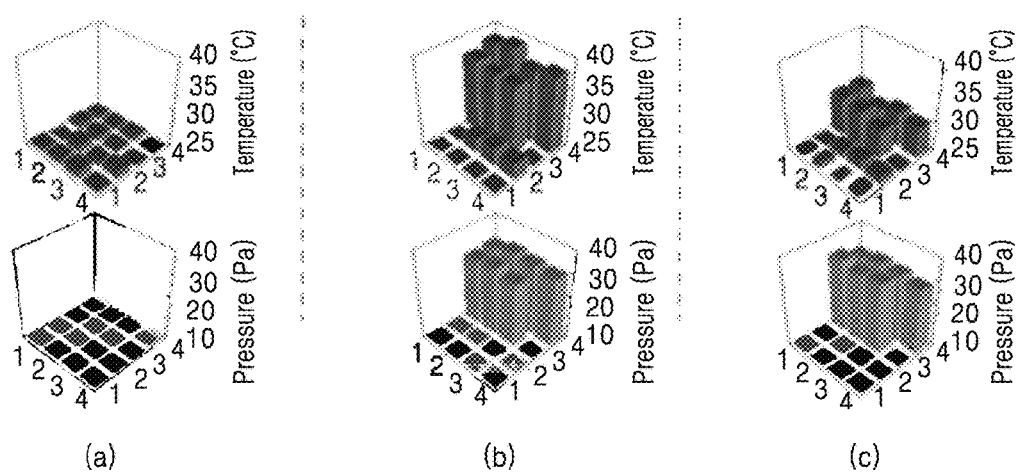
FIG. 7 illustrates graphs (a), (b), and (c) for explaining an operation of flexible bimodal sensor array according to an exemplary embodiment.

FIG. 7 illustrates graphs for explaining an operation of flexible bimodal sensor array according to an exemplary embodiment. The flexible bimodal sensor array according to the current exemplary embodiment respectively include flexible bimodal sensors disposed in a 4×4 matrix on a flexible substrate.

Referring to graph (a) of FIG. 7, temperatures and pressures that are measured by using the flexible bimodal sensor array are uniform in each of the flexible bimodal sensors.

Referring to graph (b) of FIG. 7, temperatures and pressures are measured by the flexible bimodal sensors on which a material of 40° C. is placed. As shown in the graph (b), the temperatures and pressures increase.

Referring to graph (c) of FIG. 7, when the temperatures and pressures are measured after cooling the material placed on the flexible bimodal sensor array for 30 minutes, the pressures become similar to of the pressures in graph (b), but the temperatures become lowered.

From the results of FIG. 7, it may be understood that the flexible bimodal sensor array according to the current exemplary embodiment simultaneously measures temperatures and pressures.

Figure 8:
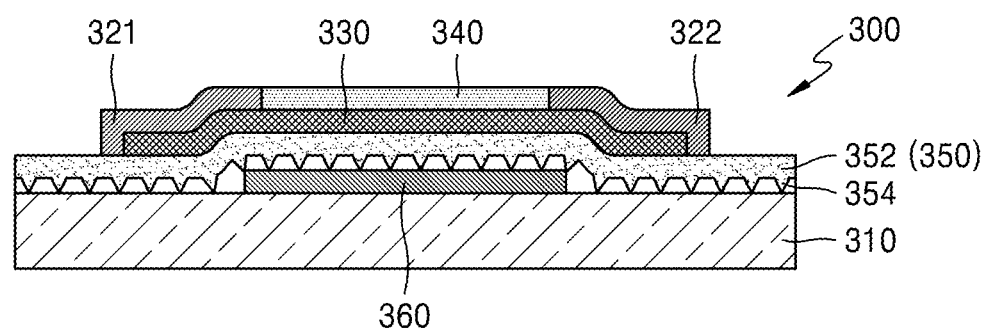
FIG. 8 is a schematic cross-sectional view of a flexible bimodal sensor including microstructure according to another exemplary embodiment.

FIG. 8 is a schematic cross-sectional view of a flexible bimodal sensor 300 including microstructure according to another exemplary embodiment. Like reference numerals or names are used to indicate elements that are substantially identical to the elements of the flexible bimodal sensor 100 of FIG. 1, and thus the detailed description thereof will not be repeated.

Referring to FIG. 8, the flexible bimodal sensor 300 includes a gate electrode 360 formed on a flexible substrate 310. A gate insulating layer 350 is formed on the gate electrode 360. The gate insulating layer 350 includes a base 352 having a predetermined thickness and a plurality of protrusions 154 extending from the base 352 toward the flexible substrate 310 and the gate electrode 360. The protrusions 354 may be in contact with the flexible substrate 310 and the gate electrode 360. A channel layer 330 is formed on the gate insulating layer 350. A source electrode 321 and the drain electrode 322 are respectively formed on both edges of the channel layer 330. An encapsulating layer 340 may be formed on the channel layer 330. The encapsulating layer 340 may cover the channel layer 330. The exemplary embodiment is not limited thereto. For example, the encapsulating layer 340 may also cover the source electrode 321 and the drain electrode 322 within the channel layer 330.

In FIG. 8, the protrusions 354 of the gate insulating layer 350 are formed to be in contact with the gate electrode 360 and the flexible substrate 310, but the current exemplary embodiment is not limited thereto. For example, the protrusions 354 may be formed to contact the channel layer 330.

Figure 9:
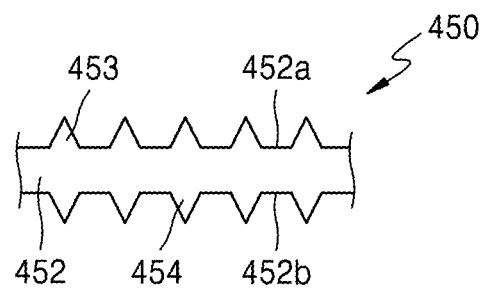
FIG. 9 is a cross-sectional view of a microstructure of a flexible bimodal sensor according to another exemplary embodiment.

FIG. 9 is a cross-sectional view of a microstructure of a flexible bimodal sensor according to another exemplary embodiment. Referring to FIG. 9, a gate insulating layer 450 of the flexible bimodal sensor includes a base 452, a plurality of first protrusions 453 formed on a first surface 452a of the base 452, and a plurality of second protrusions 454 formed on a second surface 452b of the base 452. The second surface 452b faces the first surface 452a.

The gate insulating layer 150 of FIG. 1 or the gate insulating layer 350 of FIG. 8 may be substituted by the gate insulating layer 450.

The flexible bimodal sensor that employs the gate insulating layer 450 may have a larger deformation with respect to physical stimulations than the flexible bimodal sensors 100 or 300, and thus, the sensitivity of the flexible bimodal sensor including the gate insulating layer 450 may be increased.

The flexible bimodal sensor according to the exemplary embodiments may have a high sensitivity to the extent that a human pulse wave can be measured, and two physical stimulations may be measured by using a single sensor. A plurality of flexible bimodal sensors may be disposed on a flexible substrate in an array, and the flexible bimodal sensor array may be applied to a wearable device or an electronic skin.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A flexible bimodal sensor comprising:
a gate electrode;
a flexible substrate;
a source electrode disposed on the flexible substrate;
a drain electrode disposed on the flexible substrate apart from the source electrode;
a channel layer disposed on the source electrode and the drain electrode and a portion of the flexible substrate between the source electrode and the drain electrode; and
a gate insulating layer comprising a plurality of protrusions, the gate insulating layer being disposed on the channel layer and arranged between the channel layer and the gate electrode and,
wherein the drain electrode outputs a current signal simultaneously indicating a temperature value and a pressure value sensed by the flexible bimodal sensor, and
the gate insulating layer comprises a base having a predetermined thickness and the plurality of protrusions extends from a first surface of the base towards the channel layer.

2. The flexible bimodal sensor of claim 1, wherein the channel layer comprises one of silicon, an organic semiconductor, and a semiconductor oxide.

3. The flexible bimodal sensor of claim 2, further comprising an encapsulating layer that covers the channel layer and is disposed between the channel layer and the gate insulating layer.

4. The flexible bimodal sensor of claim 3, wherein the encapsulating layer comprises one of an organic material comprising tetratetracontane (TTC) or methylcycloheane (MCH), an inorganic oxide comprising $Al_2O_3$ or $HfO_2$, and a stack structure in which the organic material and the inorganic oxide are stacked.

5. The flexible bimodal sensor of claim 1, wherein the plurality of protrusions further comprise a plurality of first protrusions formed on a second surface of the base facing the first surface of the base.

6. The flexible bimodal sensor of claim 4, wherein the gate insulating layer comprises a first material selected from the group consisting of P(VDF_TrFE), P(VDF-TrFE-CFE), P(VDF-TrFE-CtFE), polydimethylsiloxane (PDMS), and polyurethane (PU).

7. The flexible bimodal sensor of claim 6, wherein the gate insulating layer further comprises inorganic nanoparticles distributed in the first material.

8. The flexible bimodal sensor of claim 1, wherein the plurality of protrusions of the gate insulating layer has a pyramid shape or a truncated pyramid shape.

9. The flexible bimodal sensor of claim 1, wherein the flexible bimodal sensor includes a plurality of bimodal sensors arranged in a matrix shape on the flexible substrate.

10. A flexible bimodal sensor comprising:
a flexible substrate;
a gate electrode disposed on the flexible substrate;
a gate insulating layer covering the gate electrode on the flexible substrate;
a channel layer disposed on the gate insulating layer; and
a source electrode disposed on the channel layer; and
a drain electrode disposed on the channel layer apart from the source electrode;
wherein the gate insulating layer comprises a plurality of protrusions, and
wherein the drain electrode outputs a current signal simultaneously indicating a temperature value and a pressure value measured by the flexible bimodal sensor, and the gate insulating layer comprises a base having a predetermined thickness and the plurality of protrusions extends from a first surface of the base towards the channel layer.

11. The flexible bimodal sensor of claim 10, wherein the channel layer comprises silicon, an organic semiconductor, or a semiconductor oxide.

12. The flexible bimodal sensor of claim 11, further comprising an encapsulating layer that covers the channel layer, the drain electrode, and the source electrode.

13. The flexible bimodal sensor of claim 12, wherein the encapsulating layer comprises one an organic material comprising tetratetracontane (TTC) or methylcycloheane (MCH), an inorganic oxide comprising $Al_2O_3$ or $HfO_2$, and a stack structure in which the organic material and the inorganic oxide are stacked.

14. The flexible bimodal sensor of claim 10, wherein the plurality of protrusions further comprise a plurality of protrusions on a second surface of the base facing the first surface of the base.

15. The flexible bimodal sensor of claim 13, wherein the gate insulating layer comprises a first material selected from the group consisting of P(VDF_TrFE), P(VDF-TrFE-CFE), P(VDF-TrFE-CtFE), polydimethylsiloxane (PDMS), and polyurethane (PU).

16. The flexible bimodal sensor of claim 15, wherein the gate insulating layer further comprises inorganic nanoparticles distributed in the first material.

17. The flexible bimodal sensor of claim 10, wherein the plurality of protrusions of the gate insulating layer has a pyramid shape or a truncated pyramid shape.

18. The flexible bimodal sensor of claim 10, wherein the flexible bimodal sensor includes a plurality of bimodal sensors arranged in a matrix type on the flexible substrate.

* * * * *